United States Patent
Miura et al.

(10) Patent No.: US 7,300,763 B2
(45) Date of Patent: Nov. 27, 2007

(54) METHOD OF TESTING MYELOTOXICITY WITH THE USE OF FLOW CYTOMETER

(75) Inventors: Daishiro Miura, Tokyo (JP); Shoko Ogata, Tokyo (JP); Yukiya Koike, Tokyo (JP)

(73) Assignee: Teijin Limited, Osaka (JP)

( * ) Notice: Subject to any disclaimer, the term of this patent is extended or adjusted under 35 U.S.C. 154(b) by 616 days.

(21) Appl. No.: 10/297,749

(22) PCT Filed: Jun. 8, 2001

(86) PCT No.: PCT/JP01/04871

§ 371 (c)(1),
(2), (4) Date: Dec. 9, 2002

(87) PCT Pub. No.: WO01/94936

PCT Pub. Date: Dec. 13, 2001

(65) Prior Publication Data

US 2003/0148405 A1    Aug. 7, 2003

(30) Foreign Application Priority Data

Jun. 8, 2000    (JP) ............................. 2000-171928

(51) Int. Cl.
*G01N 33/567* (2006.01)

(52) U.S. Cl. .................. 435/7.21; 435/7.24; 435/325; 435/343; 435/352; 435/353; 435/354; 436/517; 436/17; 436/63; 436/172; 424/9.2; 422/68.1; 422/73; 422/82.05

(58) Field of Classification Search ............... 435/7.21, 435/7.23, 7.24, 7.25, 40.5, 441, 325, 343, 435/352–354, 286.5, 287.1; 436/517, 521, 436/17, 63, 64; 424/9.2; 422/68.1, 73, 82.05
See application file for complete search history.

(56) References Cited

U.S. PATENT DOCUMENTS 5,137,809 A * 8/1992 Loken et al. ............... 435/7.21
6,100,038 A * 8/2000 Dertinger et al. ............... 435/6

FOREIGN PATENT DOCUMENTS

| JP | 1-161153 A | 8/1992 |
| JP | 6-27017 A | 2/1994 |
| WO | WO 95/5012813 A | 5/1995 |

OTHER PUBLICATIONS

Dertinger et al., Flow Cytometric analysis of micronucleated reticulocytes in mouse bone marrow, Mutation Research 390: 257-262 (1997).*
Jefferies et al., Analysis of Lymphopoietic Stem Cells with a Monoclonal Antibody to the Rat Transferrin Receptor, Immunology, 54: 333-341 (1985).*
Kenji Kishihara, "CD45 to Lymph-Kyu no Bunka Kasseika", Medical Immunology, vol. 27, No. 1, pp. 61 to 71, (1994).

Stephen D. Dertinger, et al., "Flow cytometric analysis of micronucleated reticulocytes in mouse bone marrow", Mutation Research, 390, (3), pp. 257 to 262, (1997).
David G. Campbell, et al. "Rat Brain Thy-1 Glycoprotein", *Biochem. J.* (1981), vol. 195; pp. 15-30.
Alan F. Williams, et al., "Similarities in Sequences and Cellular Expression Between Rat CD2 and CD4 Antingens", *J. Exp. Med.*, (Feb. 1987), vol. 165, pp. 368-380.
F.G.M. Kroese, et al., "Monoclonal Antibodies to Rat B Lymphocyte (Sub) Populations", *Adv. Exp. Med. Biol.* (1981), vol. 195, pp. 15-30.
W.A. Jefferies, et al., "Analysis of Lymphopoietic Stem Cells with a Momoclonal Antibody to the Rat Transferrin Receptor", *Immunology* (1985), vol. 54, pp. 333-341.
Takuya Tamatani, et al., "Characterization of the Rat Leukocyte Integrin, CD11/CD18, by the use of LFA-1 Subunit Specific Monoclonal Antibodies", *Eur. J. Immunol.* (1991), vol. 21, pp. 627-633.
Takuya Tamatani, et al., "Characterization of Rat LECAM-1 (L-Selection) by the use of Monoclonal Antibodies and Evidence for the Presence of Soluble LECAM-1 in Rat Sera", *Eur. J. Immunol.* (1993), vol. 23, pp. 2181-2188.
Christopher A. Sunderland, et al., "Purification with Monoclonal Antibody of a Predominant Leukocyte-Common Antigen and Glycoprotein from Rat Thymocytes", *Eur. J. Immunol.* (1979), vol. 9, pp. 155-159.
Roger J. Brideau, et al., "Two Subsets of Rat T Lymphocytes Defined with Monoclonal Antibodies", *Eur. J. Immunol.* (1980), vol. 10, pp. 609-615.
Phillip Ruiz, et al., "Cytofluorographic Evidence that Thymocyte Dipeptidyl Peptidase IV (CD26) Activity is Altered with Stage of Ontogeny and Apoptotic Status", *Cytometry* (1996), vol. 23, pp. 322-329.
J. Malin-Berdel, et al., "Flow Cytometric Determination of Esterase and Phosphatase Activities and Kinetics in Hematopoietic Cells with Fluorogenic Substrates", *Cytometry* (1979), vol. 1, No. 3, pp. 222-228.
Daishiro Miura, et al., "Basic Examination of Reticulocytes Count Using the Flow-cytometer (EPICS XL): A Comparative Study Between Flow-cytometer Method and Conventional Method Using Hemolytic-anemia Animals", (Proceedings of the 26th Annual Meeting, *The Journal of Toxicological Sciences* (1999), vol. 24, No. 4, p. 306.

* cited by examiner

*Primary Examiner*—Gailene R. Gabel
(74) *Attorney, Agent, or Firm*—Sughrue Mion Pllc.

(57) ABSTRACT

The objects of the present invention are to solve low test efficiency and low accuracy which are problems encountered in the conventional methods for testing myelotoxicity of a drug by observing smears. To this end, markers for discriminating and identifying hematopoietic stem cells and blood cells at various differentiation stages in bone marrow are identified. From this point of view, cell surface antigens are specified. Thus, it is found that the myelotoxicity of a drug can be evaluated with a high efficiency at a high accuracy by using flow cytometry to analyze for a change in the quantity of bone marrow-derived cells expressing the cell surface antigens after administration of the drug to an animal.

8 Claims, No Drawings

METHOD OF TESTING MYELOTOXICITY WITH THE USE OF FLOW CYTOMETER

TECHNICAL FIELD

The present invention relates to a method for evaluating and testing toxicity of drugs to hematopoiesis in bone marrow by analyzing the quantity of expression of cell surface antigens of bone marrow cells using a flow cytometer.

BACKGROUND ART

Blood cells are produced from cells called hematopoietic stem cells through a process of proliferation and differentiation. The hematopoietic stem cells and blood cells at various differentiation stages are present in bone marrow. The discrimination and identification of the hematopoietic stem cells and blood cells in bone marrow and examining the change of the number or ratio thereof are scientifically and industrially significant for evaluating the toxicity of a drug including a medicine to the hematopoiesis in bone marrow.

In order to evaluate the toxicity to the hematopoiesis, it is necessary to discriminate and identify the hematopoietic stem cells and blood cells in bone marrow and clarify what actions occur in each lineage or differentiation stage. It is thought that there is a possibility of changing the number of erythroblasts and reticulocytes, for example in the case of drugs having toxicity to erythrocytes and varying the number of myelocytes (myeloblasts, promyelocytes, myelocytes, metamyelocytes or the like) or lymphocytes present in bone marrow in the case of drugs acting on leukocytes (lymphocytes, granulocytes or the like).

A method for preparing a smear, morphologically discriminating cells with human eyes by microscopic observation and identifying the cells has hitherto been mainly used for evaluating the toxicity to the hematopoiesis in bone marrow. The smear is prepared by thinly smearing a collected bone marrow sample on a slide glass and used by usually subjecting the smear to May-Grünwald and Giemsa staining or the like, then observing cell morphology under an optical microscope and determining how the ratio of respective cells varies. However, it is necessary to observe a large number of cells by a skilled person in charge of tests for evaluating the toxicity by the method and there are many subjects in the method in aspects of quality and quantity of date and time. Therefore, establishment of a method by which the problems can be overcome has been desired.

Flow cytometers have been utilized for collecting various qualitative or quantitative parameters in individual cells in fields of studies on cell biology, immunology and hematology. The flow cytometers are apparatuses designed to keep cells in a state of a suspension, passing the suspension through a fluid system at a high speed, instantaneously analyzing optical and electric signals obtained from the respective cells through a detecting part and studying and elucidating biological features of the respective cells. For example, the flow cytometers are utilized for measurement of the nucleic acid amount, enzyme activity, calcium influx, cell membrane potential, pH and the like (Malin-Berdel, J. and Valet, G. 1980. Cytometry 1:222-228; Phillip, R. et al. 1995. Cytometry 23: 322-329). It is known that the blood cells can be discriminated and identified by determining the quantity of expression of a cell surface antigen characteristic to each species of the cells by using the flow cytometers, for example, CD2 (Williams, A. F. et al. 1987.J. Exp. Med 165:368-380) and CD8 (Brideau, R. J. et al. 1980. Eur. J. Immunol. 10: 609-615) are known as specific for lymphocytes; CD11b is known as specific for granulocytes and myelocytes (Tamatani, T. F. et al. 1993. Eur. J. Immunol. 23: 2181-2188), CD18 (Tamatani, T. M. 1991. Eur. J. Immunol. 21: 627-633), CD45 (Sunderland, C. A. 1979. Eur. J. Immunol. 9: 155-159), CD45R.(Kroese, F. G. M. 1986, Adv. Exp. Med. Biol. 186: 81-89), CD90 (Campbell, D. G. 1981. Biochem. J. 195: 15-30) and the like are known as cell surface antigens recognized to be common to leukocytes. CD71 is known as a cell surface antigen correlating with the proliferating activity of cells (Jefferies, W. A. 1985. Immunolgy 54: 333-341).

The fact that rapid analysis can mechanically be carried out for a large number of cells with a small amount of a sample in a short time is cited as features of the method for using flow cytometers. Furthermore, the fact that the accuracy control important to assurance of data quality can be conducted and objective test data can be obtained is also cited as the features.

Johanna and Fridtjof describe the identification and isolation of respective progenitor cells of hematopoietic stem cells, myelocytes, lymphocytes and erythrocytes in normal adults or fetuses by using CD34, CD38, a cell adhesion molecule (L-selectin, CD18, CD33, CD44, CD48, CD49e, CD50 or CD52) and/or growth factor receptors (SCFR, GM-CSFR, IL-6R, gp130/IL-6R and IL-7R) as markers with flow cytometers (WO95/12813).

Terstappen describes the identification and discrimination of cell populations in peripheral blood or bone marrow in normal adults or fetuses using CD45 and CD71 as markers with flow cytometers [JP-A 6-27017 (hereunder, JP-A means "Japanese Unexamined Patent Publication")].

Loken describes the discrimination and identification of bone marrow cells in normal adults by combining CD45 with various cell surface antigens (CD15, CD16, CD10, CD34, CD20, CD19, CD14, CD3 and CD11b) with flow cytometers (JP-A 1-161153).

In the above studies, it is shown that the method with the use of flow cytometers is useful when peripheral blood cells or bone marrow cells derived from human adults or fetuses; however, it is not disclosed that the method with the use of flow cytometers is similarly useful for experimental animals.

In general, it is not thought that facts confirmed in humans about what cell surface antigens are expressed in what blood cell in a process for proliferation and differentiation stages from hematopoietic stem cells can directly be extended to other animal species.

The above reports take the hematopoietic stem cell transplantation or the like into consideration, and the discrimination and identification of specific cell populations are considered as the main purpose of utilization. In order to utilize the method with the use of flow cytometers for evaluating the toxicity of drugs, it is, however, necessary to use cell surface antigen markers suitable for the purposes as an index.

It is heretofore not clear at all whether a suitable marker is present or whether the marker is actually useful even. if the marker is present. Namely, it is necessary to elucidate the correspondence of toxicological change of the number or the ratio of specific cell populations with the drugs possessing the hematopoietic toxicity to the change of the marker in question.

The above reports do not describe whether or not the identification and discrimination of cell populations can be carried out even for bone marrow cells derived from experimental animals by analyzing the cell surface antigens as markers with flow cytometers. Furthermore, the reports do not describe whether or not the markers in the reports are useful for evaluating the toxicity of a drug to hematopoiesis in bone marrow. Accordingly, the possibility of carrying out toxicity tests using experimental animals with flow cytometers could not be foreseen even on the assumption of the above reports.

Since the cell populations in bone marrow is heterogeneous as compared with peripheral blood, it is necessary to find out cell surface antigens to be an appropriate marker for discriminating and identifying the lineage of cells or differentiation stage with the use of flow cytometers. And then, it is necessary to elucidate that the utilization of the markers is useful for evaluating toxicity of a drug to hematopoiesis in bone marrow.

The flow cytometers are heretofore scarcely utilized in fields of toxicity. tests. Absence of investigation and substantiation of practicality and usefulness essential to utilization in toxicity tests, especially lack of data on expression patterns of cell surface antigens in hematopoietic stem cells in bone marrow of experimental animals (rodents such as rats) used in the toxicity tests or blood cells at various differentiation stages is cited as main reasons.

Examples of analyzing reticulocytes in peripheral blood with a flow cytometer and reporting that the evaluation of toxicity to erythrocytic hematopoiesis can be carried out by inventors of the present invention are cited as examples of utilizing the flow cytometer in toxicity tests (Miura, D. 1999. J. Toxicol. Sci. 24: 306). In the case of reticulocytes, measurement of the amount of intracellular RNA is a useful marker for identifying cells, and the investigation and substantiation as to establishment and usefulness of the method for testing using the flow cytometer can be made. However, there is no knowledge on what markers may be used for the method for testing toxicity to bone marrow hematopoiesis, especially leukocyte hematopoiesis with the flow cytometer.

DISCLOSURE OF THE INVENTION

The inventors of the present invention consider that the above problems in the method for observing the smear which is a conventional method for testing myelotoxicity can be solved if the myelotoxicity can be examined with the use of the flow cytometer. For that purpose, it is indispensable to find out a marker so that the hematopoietic stem cells and blood cells at various differentiation stages in bone marrow can be discriminated and identified and the myelotoxicity of a drug can finally be evaluated.

As a result of intensive studies, the inventors of the present invention have found that CD45, CD45R, CD71 and CD90 as the cell surface antigens in rats which are representative experimental animals used for toxicity tests are expressed in bone marrow, and that evaluation of the toxicity of the drug to hematopoiesis in bone marrow can be made by analyzing the quantity of expression of the cell surface antigens. Thereby, the inventors of the present invention achieve the method for testing myelotoxicity with the use of a flow cytometer. Namely, the present invention is a method for evaluating the myelotoxicity of the drug with the use of the flow cytometer.

BEST MODE OF CARRYING OUT THE INVENTION

The flow cytometer suitably used in the present invention is a model widely used in studies on cell biology, immunology, hematology or the like.

The cell surface antigens suitably used in the present invention are such that expression is confirmed in blood cells in bone marrow, and examples of the cell surface antigens include CD45, CD45R, CD71, CD90 or the like.

When the expression of the cell surface antigens is measured, a specific antibody to the cell surface antigens is used. Any of serum containing an antibody, a polyclonal antibody specimen and a monoclonal antibody specimen can be used as the antibody if specificity for the cell surface antigens is confirmed.

The antibody labeled with a fluorescent dye is used. A fluorescent dye excitable with laser beams used in the flow cytometer and detectable can be, utilized as the fluorescent dye. Examples thereof include fluorescein, rhodamine or the like.

A femur, an ilium, a sternum, a costa or a rib and the like are cited as collection sites of bone marrow. Cells in bone marrow are collected by using bovine fetal serum, calf serum, a buffer solution or the like. The collected cells may directly be used for the tests or the cells subjected to hemolytic treatment or separated from erythrocytes with Percoll or ficoll may be used.

Any techniques of determining the ratios of expressing cells for expression of cell surface antigens or calculating the number of expressing cells or the like can be used when the myelotoxicity test of the drug is carried out by using the method of the present invention.

The myelotoxicity test performed by using the method of the present invention can be utilized in the toxicity test using experimental animals including, for example rodents such as rats.

EXAMPLES

Example 1

Analysis of Expression Pattern of Cell Surface Antigens in Bone Marrow Cells (1) Six-week-old male CD (SD) IGS rats purchased from Charles River Japan were used at the age of 8 weeks. During the housing period, the rats were fed with a feed for animals (Oriental Yeast Co., Ltd., CRF-1) and drinking water (well water containing 0.4% of a hypochlorite added) ad libitum.

The animals were housed in metal cages (one animal per cage) and kept under conditions of a temperature of 23±1° C. and a humidity of 55±15%.

(2) The bone marrow was collected from left and right femurs. The femurs were taken out under anaethesia with pentobarbital, and both ends of the femurs were cut. The bone marrow was then flushed out with 1 mL of fetal bovine serum using a syringe with a 25G injection needle. Bone pieces or the like were removed by using a Pasteur pipette, and cells were then collected by centrifugation (3,000 rpm for 5 minutes).

(3) To 20 μL of the cells collected in (2), was added 5 mL of a phosphate-buffer-solution (PBS). Thereby, a cell suspension was obtained.

(4) To 200 μL of the cell suspension in (3), was added 2 μg of a specific antibody to the cell surface antigen. Incubation was carried out at room temperature for 45 minutes. Mouse IgG2a anti-rat CD2, mouse IgG1 anti-rat CD8, mouse IgA anti-rat CD11b, mouse IgG1 anti-rat CD45, mouse IgG2b anti-rat CD45R, mouse IgG2a anti-rat CD71 and mouse IgG2a anti-rat CD90 were used as the antibody. Mouse IgG1, mouse IgG2a, mouse IgG2b and mouse IgA were used as the isotype control antibody. All the antibodies labeled with fluorescein (FITC) (Pharmingen.) were used as the antibody.

(5) After incubation, 1 mL of Optilyse C (Beckman Coulter.) was added, and treatment was carried out for 10 minutes to hemolyze erythrocytes. After the hemolytic treatment, 1 mL of PBS was added, and incubation was carried out at room temperature for 10 minutes.

(6) Procedures of adding 1 mL of PBS to a cell precipitation obtained by centrifugation (3,000 rpm for 5 minutes) after incubation and thereby washing the cells were repeated twice.

(7) After washing, 2 mL of PBS was added to the cell precipitation to provide a cell suspension. Analysis was carried out with the use of a flow cytometer (EPICS XL-MCL, Beckman Coulter.) The analysis was conducted by following procedures described below. Namely, gates were set in cell populations on a forward scattered light and a side scattered light cytegrams, and the distribution of fluorescence intensity with FITC was displayed for the cells in the gates by a histogram. The fluorescence detector sensitivity of the flow cytometer was adjusted with the cells treated with the isotype antibody.

(8) Table 1 shows results obtained by measuring expression of surface antigens for 30,000 bone marrow cells per individual with the flow cytometer. The ratio of cells expressing CD2, CD8 and CD11b was several %, and it was concluded that expression was scarcely found. On the other hand, it was confirmed that CD45, CD45R, CD71 and CD90 were expressed in several tens of % of the cells. Two cell populations different in quantity of expression were recognized for CD45.

TABLE 1

Expression pattern analysis of cell surface antigens of rat bone marrow cells

| Cell Surface Antigen | Ratio of Expressing Cells (%) (Individual Data) | | (Mean) |
|---|---|---|---|
| CD2 | 3.1 | 1.0 | 2.1 |
| CD8 | 2.8 | 1.4 | 2.1 |
| CD11b | 12.8 | 0.9 | 6.9 |
| CD45 | 54.2 | 58.4 | 56.3 |
| CD45R | 53.1 | 57.7 | 55.4 |
| CD71 | 41.5 | 13.5 | 27.5 |
| CD90 | 52.5 | 45.4 | 49.0 |

(9) From the above results, it was revealed that CD45, CD45R, CD71 and CD90 were expressed in rat bone marrow cells. It became clear that the cell surface antigens can be utilized for evaluating toxicity of a drug to hematopoiesis in bone marrow.

Example 2

Identification of Cells Expressing CD45, CD45R, CD71 and CD90 by Sorting (1) Rats and housing conditions thereof were according to Example 1.

(2) The collection of bone marrow and antibody treatment were according to Example 1. Mouse IgG1 anti-rat CD45, mouse IgG2b anti-rat CD45R, mouse IgG2a anti-rat CD71 and mouse IgG2a anti-rat CD90 were used as the antibody.

(3) After treatment with the antibodies, cell surface antigen-positive cells were sorted by using a flow cytometer (ALTRA, Beckman Coulter.).

(4) Cells in the sorting fraction were collected and suspended in an adequate amount of fetal bovine serum. Cytospin specimens were then prepared. The resulting specimens were double stained with May-Grünwald and Giemsa (May-Grünwald and Giemsa staining) commonly used in hematological studies in order to classify the cell morphology. Microscopic observation was carried out to calculate the cell ratio for each lineage and differentiation stage.

(5) One hundred cells per sorting fraction were observed under a microscope and classified for each lineage and differentiation stage. Table 2 shows the obtained results.

TABLE 2

Identification of cells in sorting fraction (results of observation of cytospin specimens)

| Cytospin Specimen Cell Morphology | Ratio of Cells (%) | | | | |
|---|---|---|---|---|---|
| | CD45[1]) Sorting Fraction | | CD45R Sorting Fraction | CD71 Sorting Fraction | CD90 Sorting Fraction |
| | Peak 1 | Peak 2 | | | |
| Immature Myelocytes[2]) | 33 | 7 | 3 | 11 | 16 |
| Mature Myelocytes[3]) | 51 | 3 | 2 | 2 | 2 |
| Erythroblasts | 0 | 0 | 0 | 81 | 0 |

TABLE 2-continued

Identification of cells in sorting fraction (results of observation of cytospin specimens)

| Cytospin Specimen Cell Morphology | CD45[1]) Sorting Fraction | | CD45R Sorting Fraction | CD71 Sorting Fraction | CD90 Sorting Fraction |
|---|---|---|---|---|---|
| | Peak 1 | Peak 2 | | | |
| Lymphocytes | 15 | 88 | 95 | 6 | 81 |
| Other Cell[4]) | 1 | 2 | 0 | 0 | 1 |

[1])Two cell populations different in quanity of expression were classified as Peak 1 and Peak 2 (expessioin intensity: Peak 1 <Peak 2).
[2])Neutrophilic promyelocytes, neutrophilic myelocytes and neutrophilic metamyelocytes.
[3])Segmented neutrophils and band neutrophils
[4])Eosinophiles, monocytes, unidentified cells or the like.

(6) From the above results, it was confirmed that CD 45-expressing cells (Peak 1) were mainly myelocytes, CD45-expressing cells (Peak 2), CD45R-expressing and CD90-experssing cells were mainly lymphocytes and CD71-expressing cells were mainly erythroblasts.

Example 3

Investigation on Melotoxicity of Chemotherapeutic Agent by Cell Surface Antigen Analysis (1) Rats and housing conditions thereof were according to Example 1.

(2) 5-Fluorouracil (hereinafter abbreviated to 5-FU) as a chemotherapeutic agent in a dose of 50 mg/kg/day (7.5 mg/mL, 10 mL/kg) was intravenously administered to the rats, and a physiological saline solution was used as the control substance.

(2) The administration and the bone marrow collection were carried out according to the schedule as shown in Table 3. The days of the experiment were indicated by the day of starting the administration as day 0. Groups for collecting the bone marrow on the day 0 and day 5 of the experiment were respectively set as groups administered with the control substance. Groups for collecting the bone marrow from day 1 to day 5 of the experiment were respectively set as groups administered with the 5-FU. The number of animals in each group was 3.

TABLE 3

Schedule of administration and bone marrow collection

| Group | | Days of Experiment | | | | | |
|---|---|---|---|---|---|---|---|
| Administration | Day of Bone Marrow Collection | 0 | 1 | 2 | 3 | 4 | 5 |
| Control | 0 | ■ | | | | | |
| | 5 | V | V | V | V | V | ■ |
| 5-FU | 1 | V | ■ | | | | |
| | 2 | V | V | ■ | | | |
| | 3 | V | V | V | ■ | | |
| | 4 | V | V | V | V | ■ | |
| | 5 | V | V | V | V | V | ■ |

■: Bone marrow collection
V: Administration (4) Bone marrow collection, antibody treatment and analysis with the flow cytometer were carried out according to Example 1. A flow count (Beckman Coulter.) was added to the cell suspension during the flow cytometer analysis, and a calibration region was set on the cytogram of EPIS XL-MCL to make measurement. The absolute number of the respective cell surface antigen-expressing cells was calculated. Mouse IgGI anti-rat CD45, mouse IgG2b anti-rat CD45R, mouse IgG2a anti-rat CD71 and mouse IgG2a anti-rat CD90 were used as the antibody, and mouse IgG1, mouse IgG2a and mouse IgG2b were used as the isotype control antibody.

(5) A part of bone marrow cells were suspended in an adequate amount of fetal bovine serum. An adequate amount of the resulting suspension was then dropped onto a slide glass, and a cover glass was obliquely applied to the droplet of the bovine fetal serum containing the bone marrow cells. The slide glass was directly moved to prepare smears (the wedge method). Each smear was subjected to May-Grünwald and Giemsa staining to carry out microscopic observation, and the ratio of the cells was calculated for each lineage and differentiation stage. After calculating the ratio, the resulting ratio was multiplied by the separately obtained number of bone marrow cells to determine the absolute number by observing the smear of each cell.

(6) The expression of cell surface antigens was measured for 15,000 bone marrow cells per individual with the use of the flow cytometer. Table 4 shows the obtained results.

TABLE 4

Change of number of cell surface antigen-expressing cells after administration of 5-FU

| | Group | Number of Cell Surface Antigen-expressing Cells ($\times 10^6/\mu L$) (Mean ± SD, n = 3) | | | | | |
|---|---|---|---|---|---|---|---|
| | | Day 0 | Day 1 | Day 2 | Day 3 | Day 4 | Day 5 |
| CD45 Peak 1 | Control | 1.79 ± 0.29 | | | | | 1.37 ± 0.26 |
| | 5-FU | | 1.65 ± 0.68 | 1.20 ± 0.32 | 0.34 ± 0.13 | 0.05 ± 0.02 | 0.03 ± 0.02 |
| CD45 Peak 2 | Control | 0.57 ± 0.10 | | | | | 0.52 ± 0.10 |
| | 5-FU | | 0.76 ± 0.32 | 0.82 ± 0.20 | 0.75 ± 0.25 | 0.64 ± 0.24 | 0.51 ± 0.06 |
| CD45R | Control | 1.88 ± 0.32 | | | | | 1.58 ± 0.24 |
| | 5-FU | | 1.54 ± 0.69 | 1.46 ± 0.27 | 0.59 ± 0.11 | 0.41 ± 0.12 | 0.32 ± 0.08 |
| CD71 | Control | 1.13 ± 0.19 | | | | | 1.03 ± 0.15 |
| | 5-FU | | 0.46 ± 0.17 | 0.30 ± 0.15 | 0.09 ± 0.05 | 0.02 ± 0.02 | 0.02 ± 0.01 |

TABLE 4-continued

Change of number of cell surface antigen-expressing cells
after administration of 5-FU Number of Cell Surface Antigen-expressing Cells (×10⁶/μL)
(Mean ± SD, n = 3)

| | Group | Day 0 | Day 1 | Day 2 | Day 3 | Day 4 | Day 5 |
|---|---|---|---|---|---|---|---|
| CD90 | Control | 1.70 ± 0.35 | | | | | 1.60 ± 0.41 |
| | 5-FU | | 1.76 ± 0.79 | 1.58 ± 0.18 | 0.49 ± 0.10 | 0.16 ± 0.06 | 0.09 ± 0.02 |

The number of CD45 (Peak 1)-expressing cells began decreasing in a period between day 1 and day 2 of the experiment and was decreased to such an extent of the scarcely observed expressing cells on day 4 of the experiment. A slight decrease was observed in the number of CD90-expressing cells on day 2 of the experiment, and the number was markedly decreased on day 3 of the experiment and thereafter. A slight decrease was observed in the number of CD45R-expressing cells on day 2 of the experiment, and the decrease continued on day 3 of the experiment and thereafter. However, the extent of decrease was slight as compared with that of CD45 (Peak 1)-expressing cells or CD90-expressing cells. On the other hand, a decrease was observed in the number of CD71-expressing cells from day 1 of the experiment, and the number was decreased to such an extent of the scarcely observed expressing cells on day 3 of the experiment and thereafter. A decrease was not observed in the number of CD45 (Peak 2)-expressing cells at all.

(7) Observation of smears was carried out for 500 bone marrow cells per individual (one smear). Table 5 shows the obtained results.

ment, but the number was decreased on day 3 of the experiment and thereafter.

(8) The detection of a decrease in immature myelocytes, a decrease in erythroblasts and a decrease in lymphocytes is an especially important item for evaluating toxicity of a drug to hematopoiesis in bone marrow. Summarizing of the results shown in Tables 4 and 5, it turned out that the change of the immature myelocytes corresponded to the change of CD45 (Peak 1), the change of erythroblasts corresponded to the change of CD71 and the change of the lymphocytes corresponded to the change of CD45R or CD90.

(9) In comparison of time to obtain data shown in Table 4 or 5, about 20 seconds per individual (15,000 bone marrow cells) were required when the expression of the cell surface antigens was evaluated with the use of the flow cytometer. In contrast to this, about 10 to 20 minutes per individual (500 bone marrow cells) were required for observation of smears.

(10) From the above results, it is revealed that the change of cell surface antigens in which expression was confirmed in bone marrow cells is correlated with the expression of myelotoxicity.

TABLE 5

Results of observation on smears of bone marrow in
rats administered with 5-FU

Number of Cells (×10⁶/μL)
(Mean ± SD, n = 3)

| | Group | Day 0 | Day 1 | Day 2 | Day 3 | Day 4 | Day 5 |
|---|---|---|---|---|---|---|---|
| Immature Myelocytes | Control | 0.31 ± 0.09 | | | | | 0.33 ± 0.10 |
| | 5-FU | | 0.20 ± 0.10 | 0.09 ± 0.04 | 0.003 ± 0.001 | — | — |
| Mature Myelocytes | Control | 0.25 ± 0.08 | | | | | 0.28 ± 0.02 |
| | 5-FU | | 0.49 ± 0.22 | 0.95 ± 0.32 | 0.39 ± 0.03 | 0.12 ± 0.02 | 0.03 ± 0.01 |
| Erythroblasts | Control | 1.28 ± 0.15 | 1.00 ± 0.23 | | | | |
| | 5-FU | | 0.18 ± 0.07 | 0.02 ± 0.03 | 0.003 ± 0.001 | 0.001 ± 0.001 | — |
| Lymphocytes | Control | 1.40 ± 0.28 | | | | | 0.99 ± 0.21 |
| | 5-FU | | 2.01 ± 0.86 | 1.46 ± 0.21 | 0.62 ± 0.13 | 0.56 ± 0.20 | 0.51 ± 0.08 |

Mature myelocytes: *Neutrophilic promyelocytes, neutrophilic myelocytes* and *neutrophilic metamyelocytes*
Immature myelocytes: Segmented neutrophils and band neutrophils
—: Undetected.

A decrease was observed in immature myelocytes and erythroblasts from day 1 of the experiment, and the number was decreased to such an extent of the scarcely observed cells on day 3 of the experiment and thereafter. The number of mature myelocytes was temporarily increased from day 1 to day 3 of the experiment and then decreased on day 4 of the experiment and thereafter. On the other hand, a change was hardly observed in lymphocytes to day 2 of the experi-

INDUSTRIAL APPLICABILITY

According to the analytical method for the quantity of expression of cell antigens with the use of the flow cytometer of the present invention, the myelotoxicity of a drug can be evaluated with a higher efficiency at a higher accuracy than those of methods for observing smears.

The invention claimed is:

1. A method for evaluating the myelotoxicity of a drug hematopoiesis in bone marrow, said method comprising:

administering the drug to an animal, and measuring the number of bone marrow-derived cells that express at least one of CD45, CD45R, CD71, or CD90 by flow cytometrically analyzing CD45, CD45R, CD71, or CD90 cell surface antigen expression by the bone marrow-derived cells; and providing an indication that the drug has myelotoxicity to hematopoiesis in bone marrow when a decrease in the number of CD45, CD45R, CD71, or CD90 expressing cells, either over time or in relation to cells from untreated animals, is measured based on flow cytometric analysis of CD45 peak1, CD45R, CD71, or CD90.

2. The method according to claim 1, wherein the animal is one used in toxicity tests.

3. The method according to claim 2, wherein the animal is a rodent.

4. The method according to claim 2, wherein the animal is a rat.

5. The method according to claim 1, wherein the bone marrow-derived cells flow cytometrically measured are immature myelocytes, and wherein a decrease in the number of immature myelocytes, either over time or in relation to cells from untreated animals, based on flow cytometric analysis of CD45 peak1 is indicative of myelotoxicity to hematopoiesis in bone marrow.

6. The method according to claim 1, wherein the bone marrow-derived cells flow cytometrically measured are erythroblasts, and wherein a decrease in the number of erythroblasts, either over time or in relation to cells from untreated animals, based on flow cytometric analysis of CD71 expression is indicative of myelotoxicity of hematopiesis in bone marrow.

7. The method according to claim 1, wherein the bone marrow-derived cells flow cytometrically measured are lymphocytes, and wherein a decrease in the number of lymphocytes, either over time or in relation to cells from untreated animals, based on flow cytometric analysis of CD45R or CD90 is indicative of myelotoxicity to hematonoiesis in bone marrow.

8. The method according to claim 1, wherein:

a decrease in the number of immature myelocytes, either over time or in relation to cells from untreated animals, based on flow cytometric analysis of CD45 peak1, a decrease in the number of erythroblasts, either over time or in relation to cells from untreated animals, based on flow cytometric analysis of CD71 expression, or a decrease in the number of lymphocytes, either over time or in relation to cells from untreated animals, based on flow cytometric analysis of CD45R or CD90, is indicative of myelotoxicity of a drug to hematopoiesis in bone marrow.

* * * * *